Figure 1:
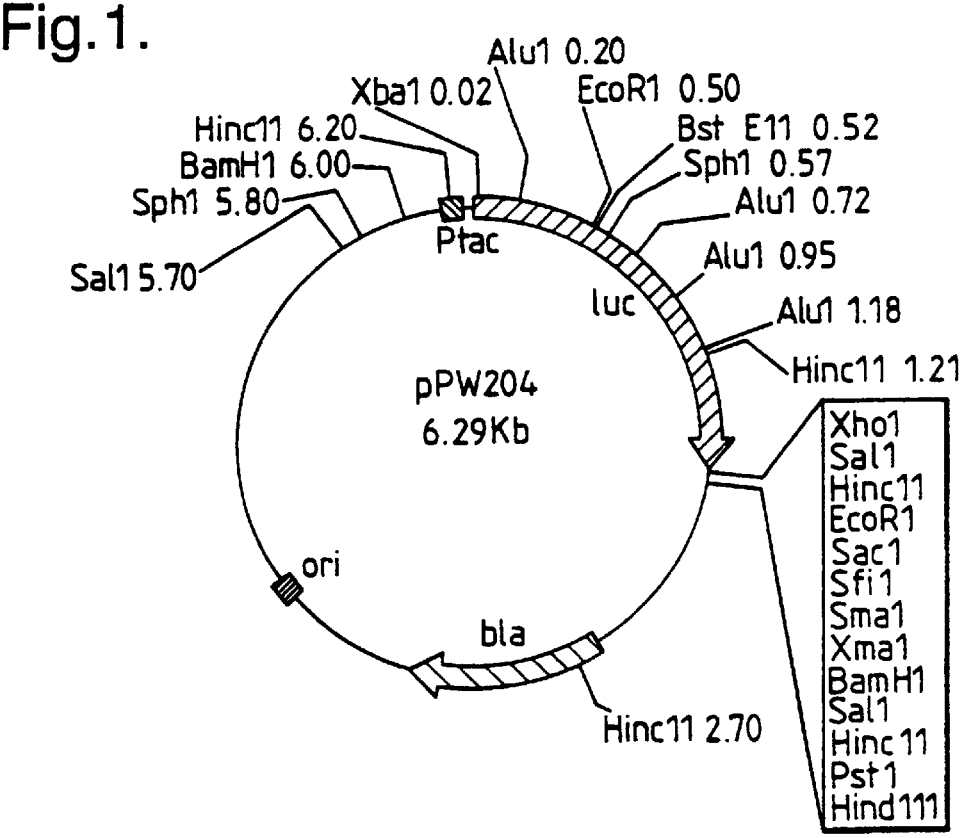

United States Patent [19]

Lowe et al.

[11] Patent Number: 6,132,983
[45] Date of Patent: Oct. 17, 2000

[54] LUCIFERASES

[75] Inventors: Christopher Robin Lowe; Peter John White; James Augusts Henry Murray, all of Cambridge; David James Squirrell, Salisbury, all of United Kingdom

[73] Assignee: The Secretary of State for Defence in Her Britannic Majesty's Government of the United Kingdom of Great Britain and Northern Ireland, London, United Kingdom

[21] Appl. No.: 08/718,425

[22] PCT Filed: Mar. 22, 1995

[86] PCT No.: PCT/GB95/00629

§ 371 Date: Nov. 20, 1996

§ 102(e) Date: Nov. 20, 1996

[87] PCT Pub. No.: WO95/25798

PCT Pub. Date: Sep. 25, 1995

[30]    Foreign Application Priority Data

Mar. 23, 1994 [GB] United Kingdom .................. 9405750
Jan. 20, 1995 [GB] United Kingdom .................. 9501170

[51] Int. Cl.$^7$ .............................. C12N 9/02; C12N 15/53; C12Q 1/66
[52] U.S. Cl. ................................. 435/8; 435/6; 435/189; 435/325; 435/348; 435/252.3; 435/252.33; 435/254.21; 435/320.1; 435/440; 536/23.2
[58] Field of Search .................................. 435/8, 189, 6, 435/172.3, 325, 348, 252.3, 252.33, 254.21, 320.1, 440; 536/23.2

[56]    References Cited

FOREIGN PATENT DOCUMENTS

A 524447  1/1993  European Pat. Off. .

OTHER PUBLICATIONS

L.G. Strause et al., "Characteristices of Luciferases From a Variety of Firefly Species: Evidence For the Presence of Luciferase Isozymes" Insect Biochem. 11(4): 417–422, 1981.

F.R. Leach et al., "Cloning and Sequencing of a Firefly Luciferase From *Photuris pennsylvanica*", Proceedings of the 9th Internation Symposium on Bioluminescence and Chemiluminescence, J.W. Hastings et al. (eds) John Wiley & Sons, Chichester England, 240–, Oct. 1996.

*Primary Examiner*—Rebecca E. Prouty
*Attorney, Agent, or Firm*—Nixon & Vanderhye PC

[57]    ABSTRACT

Proteins are provided having luciferase activity with greater heat stability than wildtype luciferases by replacing the glutamate equivalent to that at position 354 of *Photinus pyralis* luciferase or 356 of Luciola luciferases with an alternative amino acid, particularly lysine. DNA, vectors and cells that encode for and express the proteins are also provided as are test kits and reagents for carrying out luminescence assays using the proteins of the invention. Preferred proteins have a second replaced amino acid at a position equivalent to position 215 of *Photinus pyralis* luciferase or 217 of Luciola luciferases.

32 Claims, 8 Drawing Sheets

HEAT INACTIVATION OF RECOMBINANT AND WILD-TYPE (SIGMA) LUCIFERASES.
ENZYMES WERE INCUBATED FOR 20min AS DESCRIBED IN METHODS.

LUCIFERASE ACTIVITY IN CRUDE EXTRACTS OF E. COLI BL21 (DE3) pPW304
DURING GROWTH AT DIFFERENT TEMPERATURES

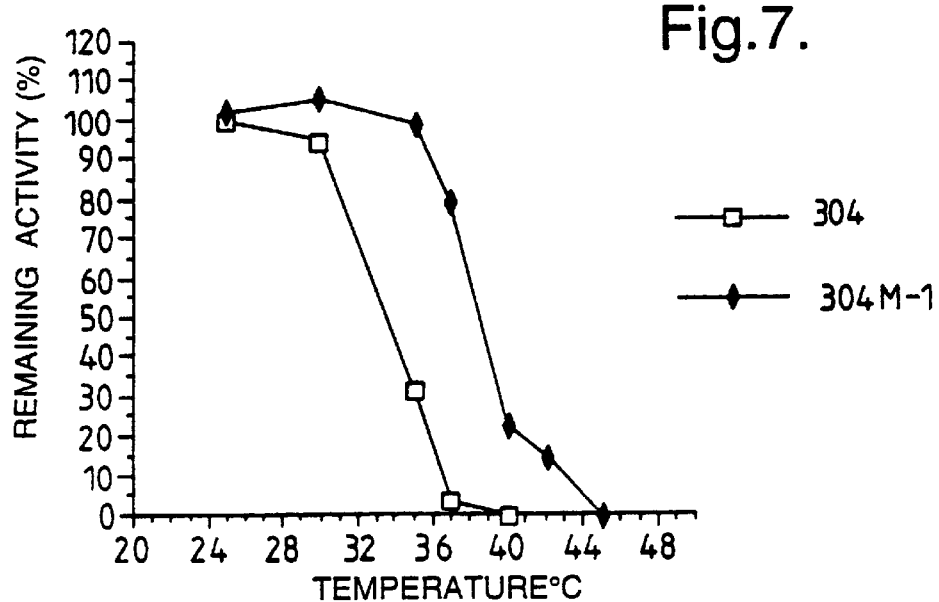
HEAT INACTIVATION OF LUCIFERASE 304 AND 304M-1.
ENZYMES WERE INCUBATED FOR 20min AS DESCRIBED IN METHODS.
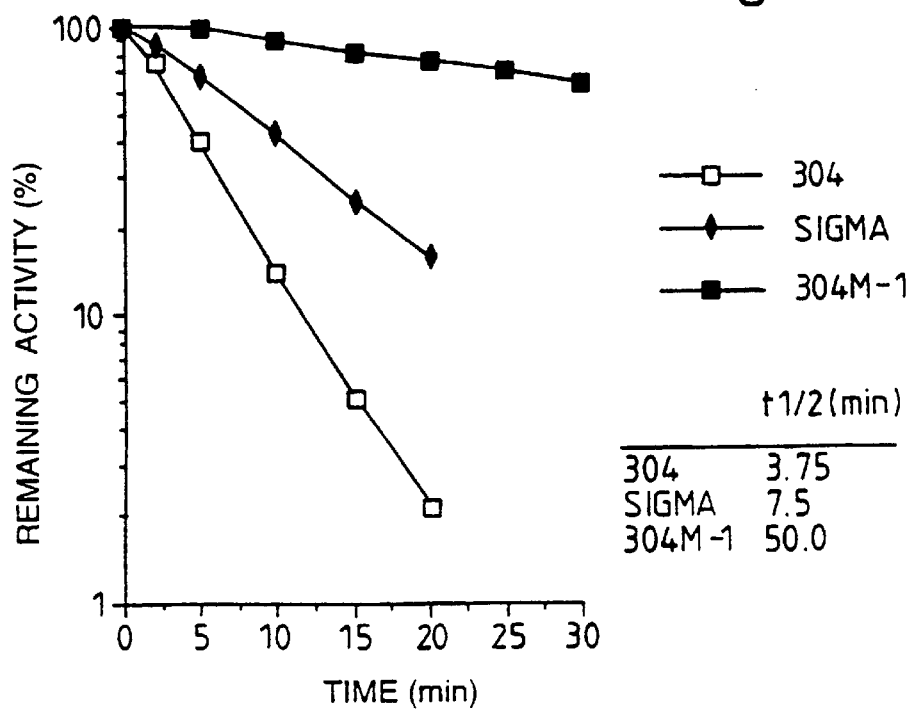
TIME DEPENDENT INACTIVATION OF LUCIFERASES AT 37°C

STABILITY OF LUCIFERASE MUTANTS AT 37°C

ENZYMES AT 10ng/ml IN HEPES, pH 7.75 CONTAINING 1% BSA AND 0.02% AZIDE

STABILITY OF LUCIFERASE MUTANTS AT 37°C

ENZYMES AT 10ng/ml IN HEPES, pH 7.75 CONTAINING 1% BSA AND 0.02% AZIDE, 2mM EDTA AND 2mM DTT

LUCIFERASES

The present invention relates to novel proteins having luciferase activity and to DNA and vectors encoding for their expression. Particularly the present invention provides luciferases having heat stability at temperatures above 30° C.

Firefly luciferase catalyses the oxidation of luciferin in the presence of ATP, $Mg^{2+}$ and molecular oxygen with the resultant production of light. This reaction has a quantum yield of about 0.88 (see DeLuca & McElroy (1978) and Seliger & McElroy (1960)) and this light emitting property has led to its use in luminometric assays where ATP levels are being measured.

Luciferase is obtainable directly from the bodies of insects such as fireflies or glow-worms or by expression from microorganisms including recombinant DNA constructs encoding for the enzyme. Four significant species of firefly from which the enzyme may be obtained, or DNA encoding for it may be derived, are the Japanese GENJI and HEIKE fireflies *Luciola cruciata* and *Luciola lateralis*, the East European Firefly *Luciola mingelica* and the North American firefly (*Photinus pyralis*). The glow-worm *Lampyris noctiluca* is a further source with the amino acid sequence of its luciferase having 84% homology to that of *Photinus pyralis*.

The heat stability of wild and recombinant type luciferases is such that they lose activity quite rapidly when exposed to temperatures in excess of about 30° C., particularly over 35° C. Such instability renders the enzyme deficient when used or stored at high ambient temperatures or if heat induced increase in reaction rate is required. It is known that Japanese firefly luciferase can be stabilised against heat inactivation by mutating it at its position 217 to replace a threonine residue by an isoleucine residue (Kajiyama & Nakano (1993) Biochemistry 32 page 13795 to 13799). In this manner the thermal and pH stability and the specific activity of the enzyme were increased. The heat stabilisation of *Photinus Dyralis* and *Luciola mingrelica* luciferases has not yet been reported.

The present inventors have now provided novel luciferases having increased heat stability over wild type luciferases by replacing a glutamate residue present in a sequence conserved in each of *Photinus pyralis, Luciola mingrelica, Luciola lateralis* and *Luciola cruciata* with alternative amino acids, particularly lysine or arginine. This glutamate is found at position 354 in *Photinus pyralis* luciferase, at the third amino acid of the conserved amino acid sequence TPEGDDKPGA found in the luciferases of this and the other species.

Thus in the first aspect of the invention there is provided a protein having luciferase activity and having over 60% homology of amino acid sequence with that of *Photinus pyralis, Luciola minzrelica, Luciola cruciata* or *Luciola lateralis* characterised in that the amino acid residue corresponding to residue 354 of *Photinus pyralis* luciferase and residue 356 of *Luciola mingrelica, Luciola cruciata* and *Luciola lateralis* luciferase is an amino acid other than glutamate.

The amino acid may be a naturally occurring amino acid or may be a so called unusual amino acid such as an modified naturally occurring amino acid or an analogue of such. Analogues of amino acids other than glutamate will be understood to be those compounds that have equivalent effect on the protein to the amino acid of which they are analogues. Typical unusual amino acids are those as set out in the US and European Patentin Manuals and the Rules of Practice in Patent Cases: application disclosures containing nucleotide and/or amino acid sequences: modified and unusual amino acids.

Preferably the protein is characterised in that it comprises an amino acid sequence XGDDKPGA wherein X is the amino acid other than glutamate. More preferably the protein comprises the amino acid sequence TPXGDDKPGA and preferably, for thermostability, X is any amino acid other than aspartic acid, proline or glycine; still more preferably it is tryptophan, valine, leucine, isoleucine or asparagine but most preferably is lysine or arginine, or analogue of any of these.

It will be realised that some species may have luciferases with one or two amino acids different in this conserved TPXGDDKPA region, but all active proteins corresponding to such luciferases that are altered to the extent that the amino acid at position three in the sequence is not glutamate are provided for by the present invention.

In preferred forms of the present invention the protein of the invention also has the amino acid at the position corresponding to amino acid 217 of the Luciola firefly luciferases or 215 of *Photinus pyralis* changed to a hydrophobic amino acid, preferably to isoleucine, leucine or valine, as described in EP 0524448 A. Such change has been found to result in an increase in thermostability over the 354 change alone; thus the two changes have effects that are substantially independent of each other and which may be used together.

In a second aspect of the invention there is provided DNA encoding for the protein of the invention and in a third aspect there is provided a vector, particularly a plasmid, comprising a luc gene (the gene encoding for luciferase) in such a form as to be capable of expressing the protein of the invention. Such forms are those where the vector includes DNA sequences capable of controlling the expression of the protein of the invention such that when incorporated into a microorganism host cell the protein may readily be expressed as required, if necessary by addition of suitable inducers.

The luc genes for *Photinus pyralis, Luciola mingrelica, Luciola cruciata* and *Luciola lateralis* are all known and isolatable by standard molecular biology techniques. *Photinus pyralis* luc gene is commercially available form Promega as the plasmid pGEM. Thus convenient methods and sources for deriving starting material for production of DNA of the invention are (i) use of naturally occurring firefly genomic DNA and amplifying the luc gene from it using eg, PCR, (ii) pGEM and (iii) pGLf37 plasmid of Kajiyama & Nakano. Further genes encoding for proteins having luciferase activity, ie. the activity of oxidising luciferin with the emission of light, will also be suitable sources for starting material for obtaining a DNA, and ultimately through gene expression, a protein of the invention.

Suitable vectors for use in manipulating wild type or other luc gene DNA in order to produce the DNA of the invention will be any vector in which the DNA can be contained within while alteration of the naturally occurring glutamate to an alternative amino acid is carried out. For chemically induced mutagenesis, eg. using agents such as hydroxylamine, this is not particularly critical and many suitable vectors will occur to those skilled in the art that will allow easy manipulation of the gene before and after the mutagenic process.

It may be preferred to specifically mutate the luc gene at the glutamate and thus a site directed mutagenesis operation will be required. Such operations may be most easily carried out in vectors and these will be well known to those skilled in the art.

For expression of luc genes of wild and known type, and those of the present invention suitable vectors include pKK223-3, pDR540 (available from Boehringer Mannheim) and pT7-7; the first two having the tac promoter under control of the lactose repressor allowing expression to be induced by presence of isopropyl-thiogalactoside (IPTG). pT7-7 allows control by the T7-RNA polymerase promoter and thus provides the basis for a very high level of gene expression in *E. coli* cells containing T7 RNA polymerase. Of these vectors expression is found to be highest when the luc genes are inserted into the pT7-7 vector.

Expression of luciferase from a Zuc gene inserted into pKK223-3 and pDR540 results in the expression of wild-type N-terminal sequence luciferase whilst expression from a luc gene inserted into pT7-7 results in synthesis of a fusion protein with extra N-terminal amino acids M-A-R-I-Q. The ribosome binding site and start codon of the luc gene in each of the vectors with the luc gene present (named constructs pPW204, pPW116 and pPW304) are shown in Table 1 of the Examples.

A third aspect of the present invention provides cells capable of expressing the proteins of the invention; methods for producing such proteins using these cells and test kits and reagents comprising the proteins of the invention. Also provided are assay methods wherein ATP is measured using luciferin/luciferase reagents, as is well known in the art, characterised in that the luciferase is a protein of the invention. Luciferase preparations of the invention are relatively thermostable at 30–70° C., particularly 37–60° C., and especially 40–50° C. as compared to the wild-type and recombinant wild-type luciferases.

Any cell capable of expressing heterologous protein using DNA sequences in its DNA, or in vectors such as plasmids contained in the cell, may be used to express the proteins of the invention. Typical of such cells will be yeast and bacterial cells such as *Saccharomyces cerevisiae* and *Escherichia coli* cells, but many other host organisms suitable for the purpose of protein expression will occur to those skilled in the art. Insect cells may be preferred as the protein is an insect protein. The protein may be expressed as a protein of similar structure to native and known recombinant luciferases, or may be expressed as a fusion or conjugate of such proteins with other amino acids, peptides, proteins or other chemical entities, eg. the M-A-R-I-Q sequence above.

It will be realised by those skilled in the art that certain hosts may have particular codon preferences, eg. bacteria in some cases use different codons to yeast, and thus the DNA incorporated into such a host may advantageously be altered to provide a degenerate codon for a given amino acid that will give more favourable expression in that host. Such degenerate DNAs are of course included in the scope of the DNA of the invention.

*E. coli* BL21(DE3) is one suitable host and has the T7 RNA polymerase integrated stably into its chromosome under control of the inducible lacUV5 promoter and is thus compatible with pT7-7 derived constructs. *E. coli* B strains like BL21 lack the lon protease and the ompT outer membrane protease. These deficiencies can help to stabilise the expression and accumulation of foreign proteins in *E. coli*. Assays of crude extracts of *E. coli* BL21(DE3) containing each of the three expression constructs described above indicated that the highest levels of expression of luciferase were obtained from cells containing the construct pPW304 (see Table 2).

The mutant proteins of the invention provide advantages other than thermostability. It has been found that the mutation of the amino acid at position Photinus 354 Luciola 356 provided a change in wavelength of light emitted on oxidation of luciferin dependent upon the amino acid or analogue with which the glutamate is substituted. Thus the invention also provides luciferases for use as specific binding agent labels or reporter genes which report back identity as a specific wavelength of light when the luciferin oxidation using their protein products; such property gives utility to such mutations as glycine. proline and aspartate. A further advantage of the proteins of the invention, deriving from their increased thermostability, is the ability to produce them at higher temperature, eg. at 37° C. or above, with correspondingly increased yield, as is exemplified below.

The proteins, DNA, vectors and cells of the invention will now be described by way of illustration only by reference to the following non-limiting Examples, Figures, Tables and Sequence listing. Further proteins, conjugates of proteins, DNA, vectors and cells, and assays and test kits incorporating any of the above will occur to those skilled in the art in the light of these.

FIGURES

FIG. 1: shows a restriction map of plasmid pPW204 derived from pKK223-3 by insertion of a luc gene as described in the Examples below.

Figure 2:
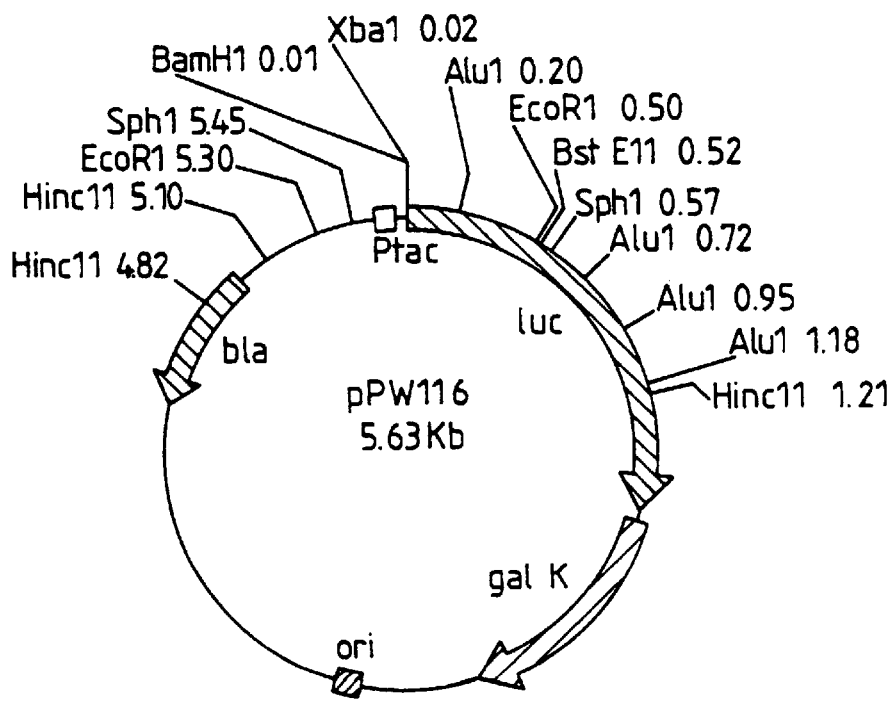

FIG. 2: shows a restriction map of plasmid pPW116 derived from pDR540 by insertion of a luc gene as described in the Examples below.

Figure 3:
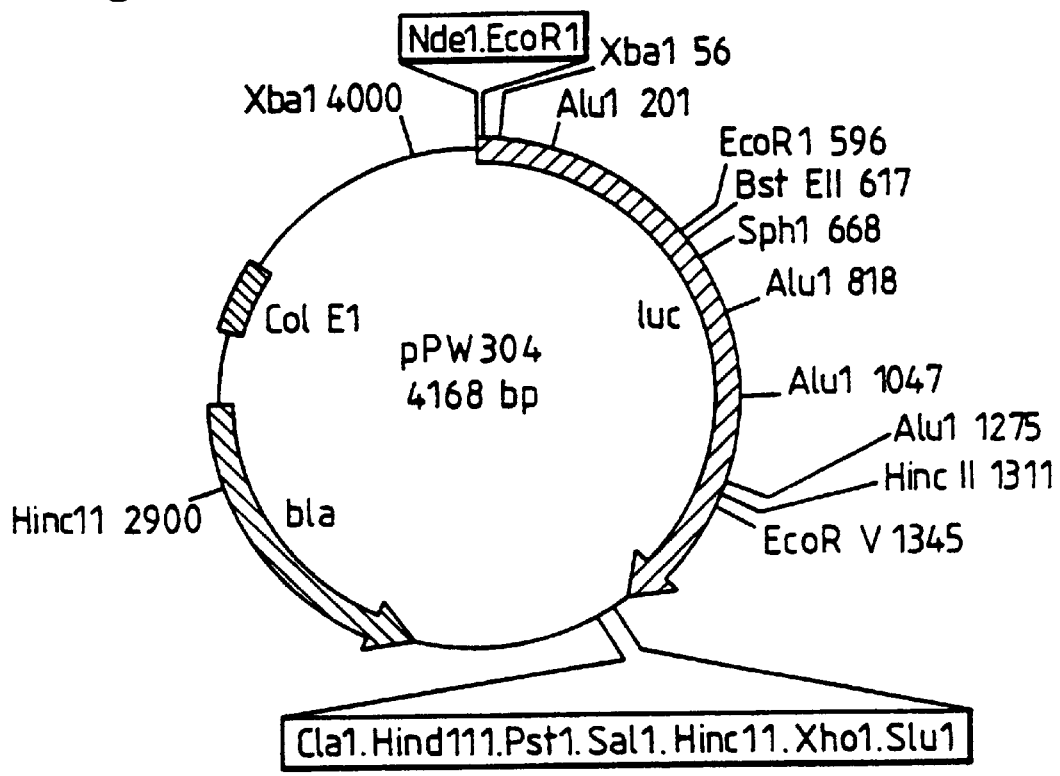

FIG. 3: shows a restriction map of plasmid pPW304 derived from pT7-7 by insertion of a luc gene as described in the Examples below.

Figure 4:
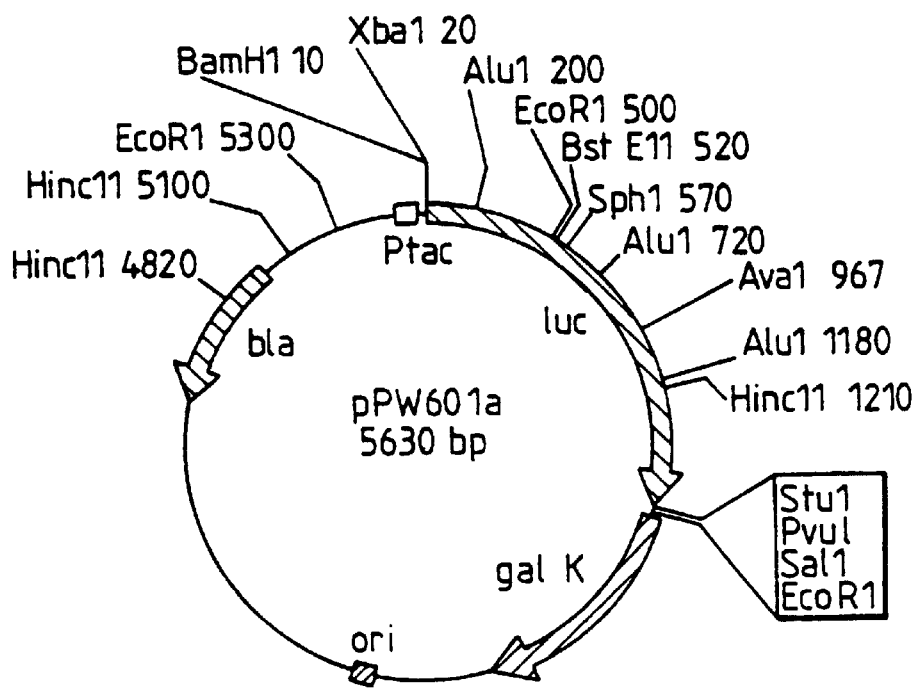

FIG. 4: shows a restriction map of plasmid pPW601a derived from pDR540 and BamH1/Sst1 fragment from pGEM-luc with the Xho site removed.

Figure 5:
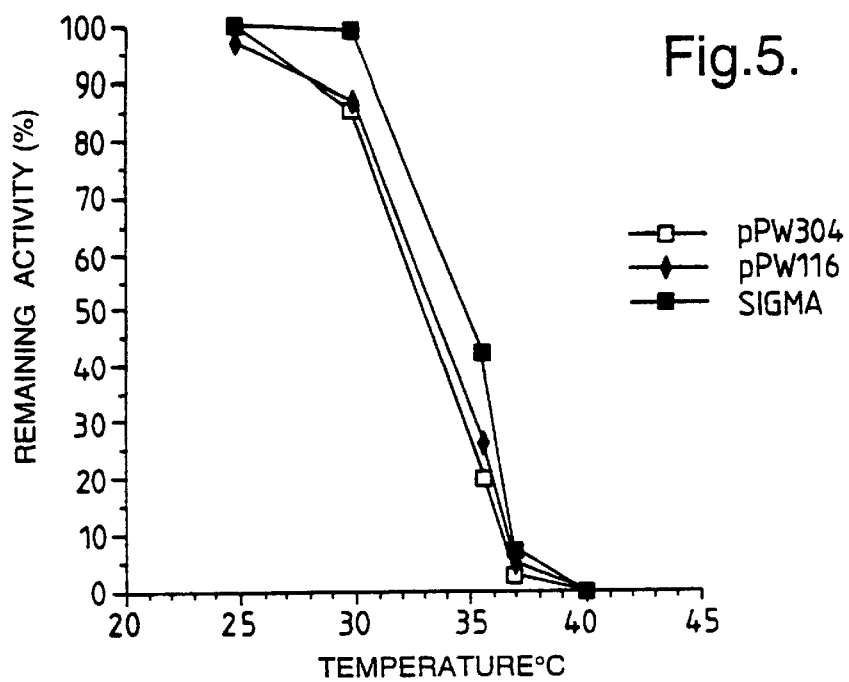

FIG. 5: shows a graph of heat inactivation of recombinant and wild type Photinus luciferases (Sigma) incubated at a given temperature for 20 minute periods as described in the Examples below.

Figure 6:
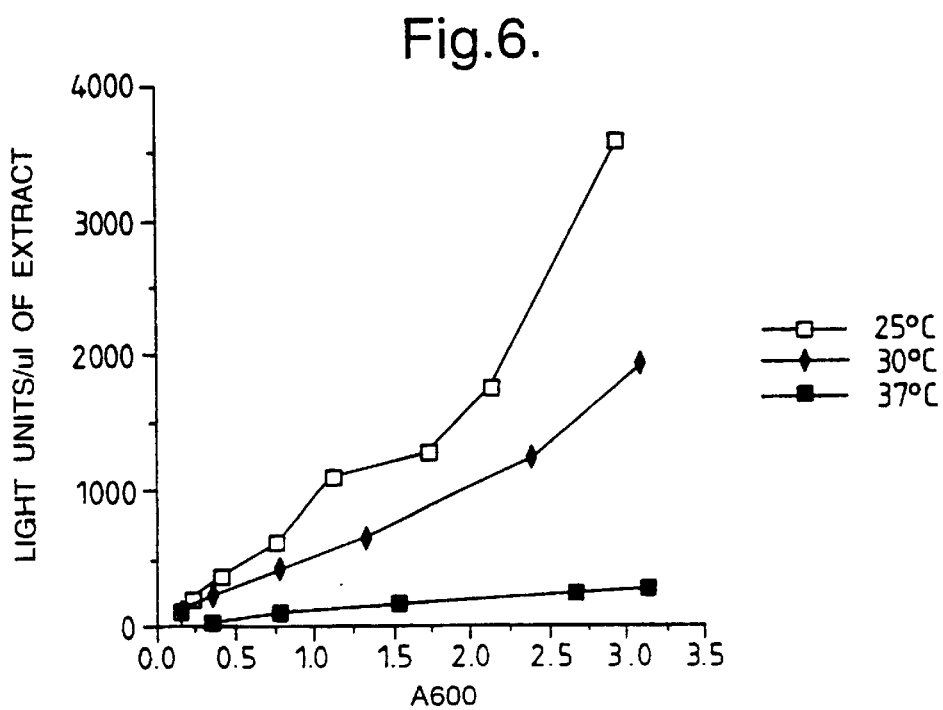

FIG. 6: shows a graph of luciferase activity in crude extracts of *E. coli* BL21(DE3)pPW304 during growth at different temperatures.

FIG. 7: shows a graph of heat inactivation of activity of luciferases derived from pPW304 and pPW304M-1 (plasmid of the invention encoding such that lysine replaces glutamate 354).

FIG. 8: shows a graph of time dependent inactivation of Sigma wild type, and pPW304 and pPW304M-1 recombinant luciferases at 37° C.

Figure 9:
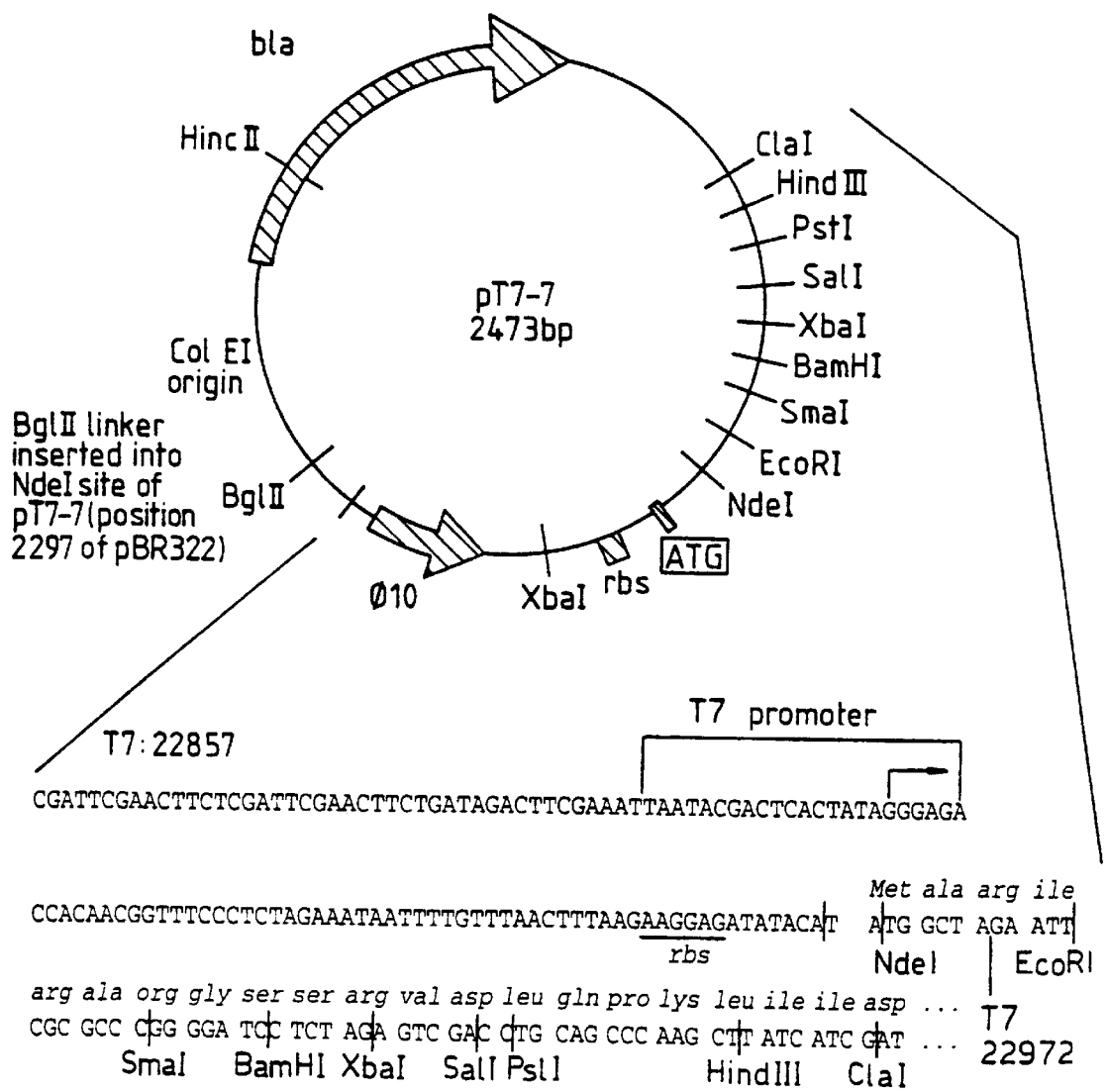

FIG. 9: shows a restriction map of pT7-7 after Tabor.

Figure 10:
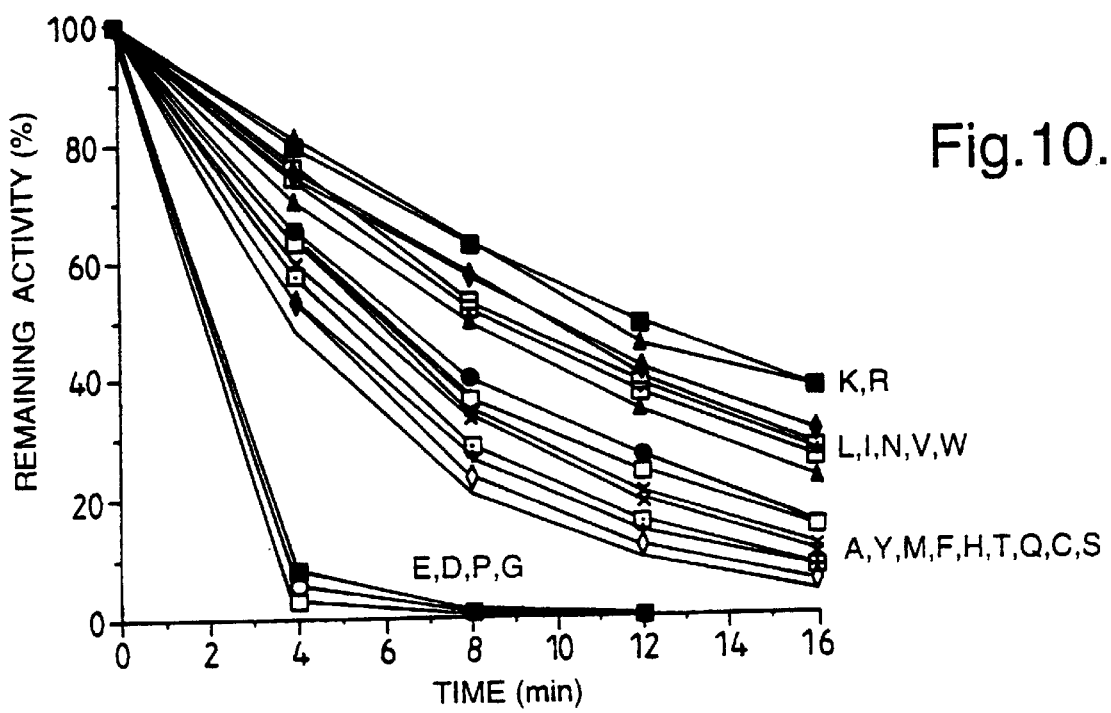

FIG. 10: shows a graph illustrating heat inactivation in Promega lysis buffer at 40° C. of activity of crude cell extracts of luciferase expressing *E. coli* of the invention expressing luciferases having substitutions of alanine, valine, leucine, isoleucine, tyrosine, phenylalanine, tryptophan, glutamine, histidine, asparagine, methionine, arginine, lysine, serine, threonine and cysteine respectively for the wild type glutamate at position 354.

Figure 11:
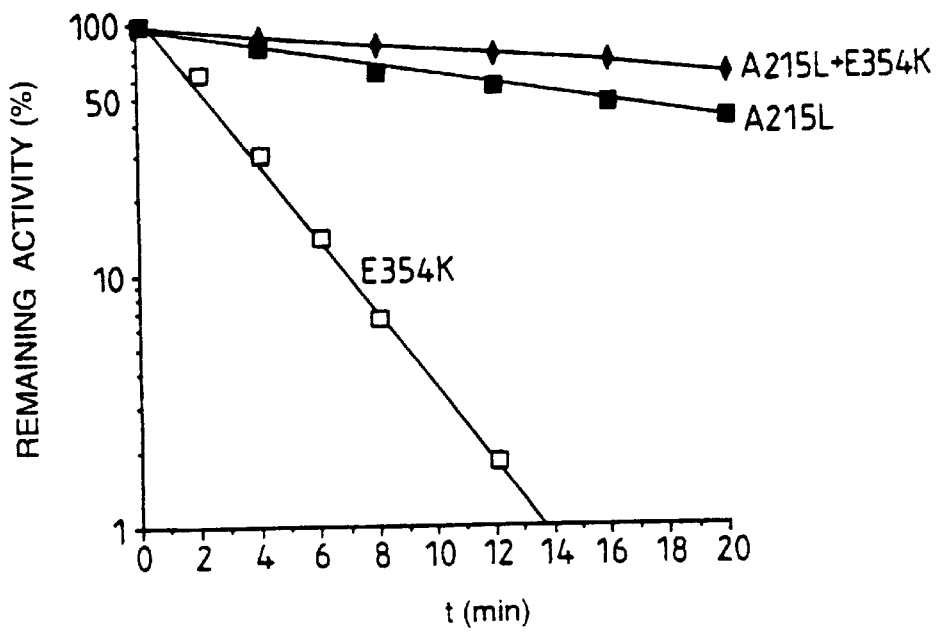

FIG. 11: shows a graph illustrating heat inactivation of activity of purified double mutant luciferase having the E354K Lysine and the A 215L Leucine changes at 47° C. in phosphate buffer as compared to the single mutants A215L and E354K.

Figure 12:
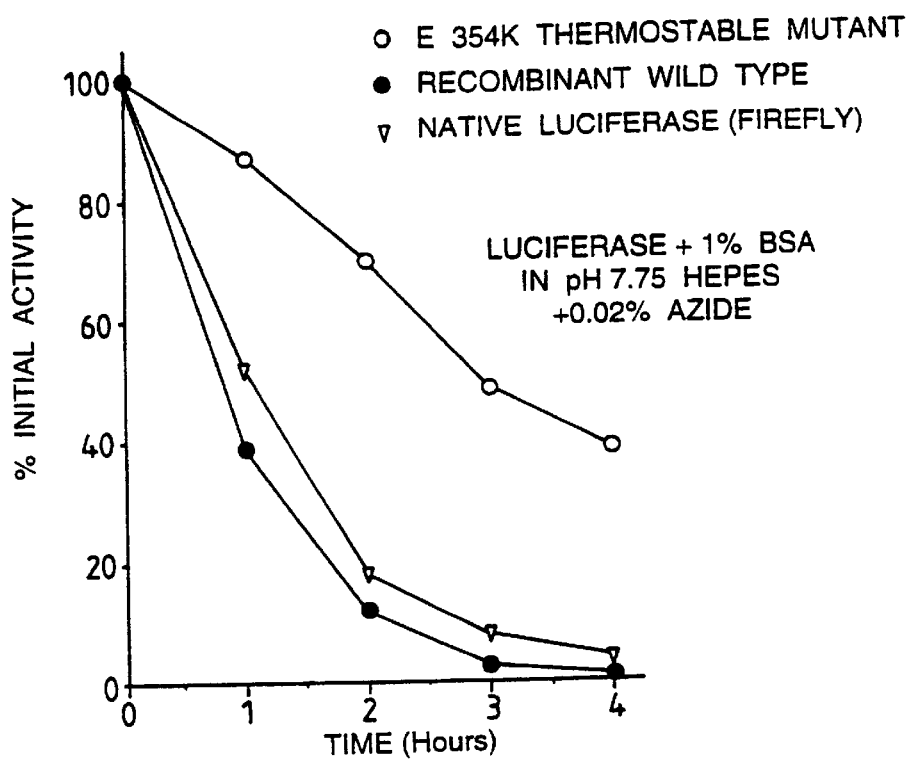

FIG. 12: shows a graph of % initial activity of the Lysine E354K mutant, recombinant wild-type and native firefly luciferases remaining against time at 37° C. in pH7.75 HEPES buffer with 0.02% azide.

Figure 13:
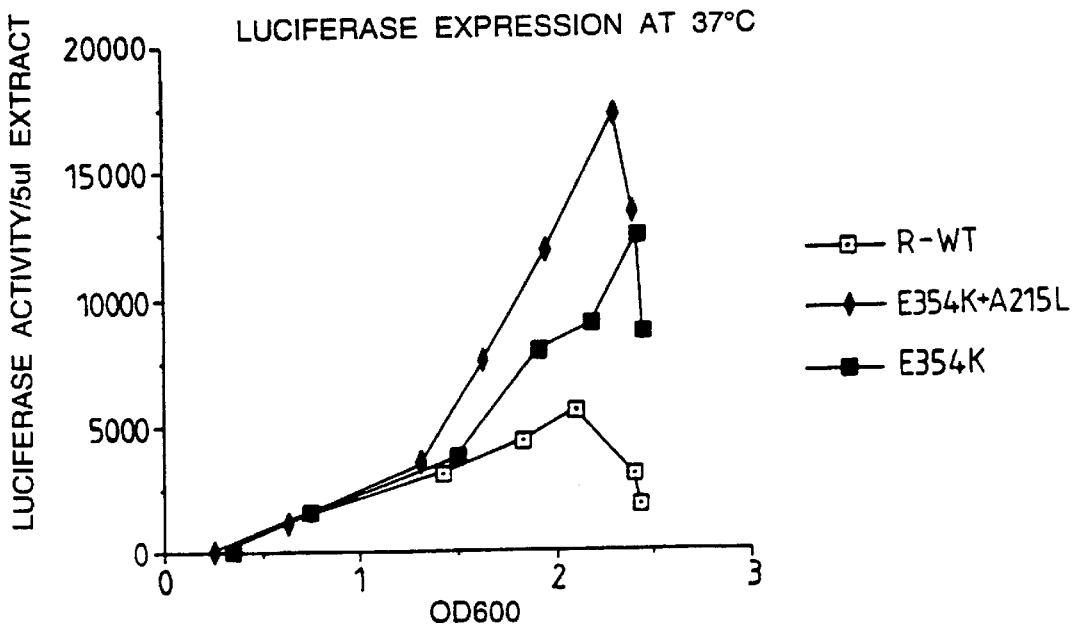

FIG. 13: shows a graph of luciferase expression at 37° C. for recombinant wild-type, E354K single and E354K+ A215L double mutants with increase in optical density as a measure of culture cell density plotted against luciferase activity.

Figure 14:
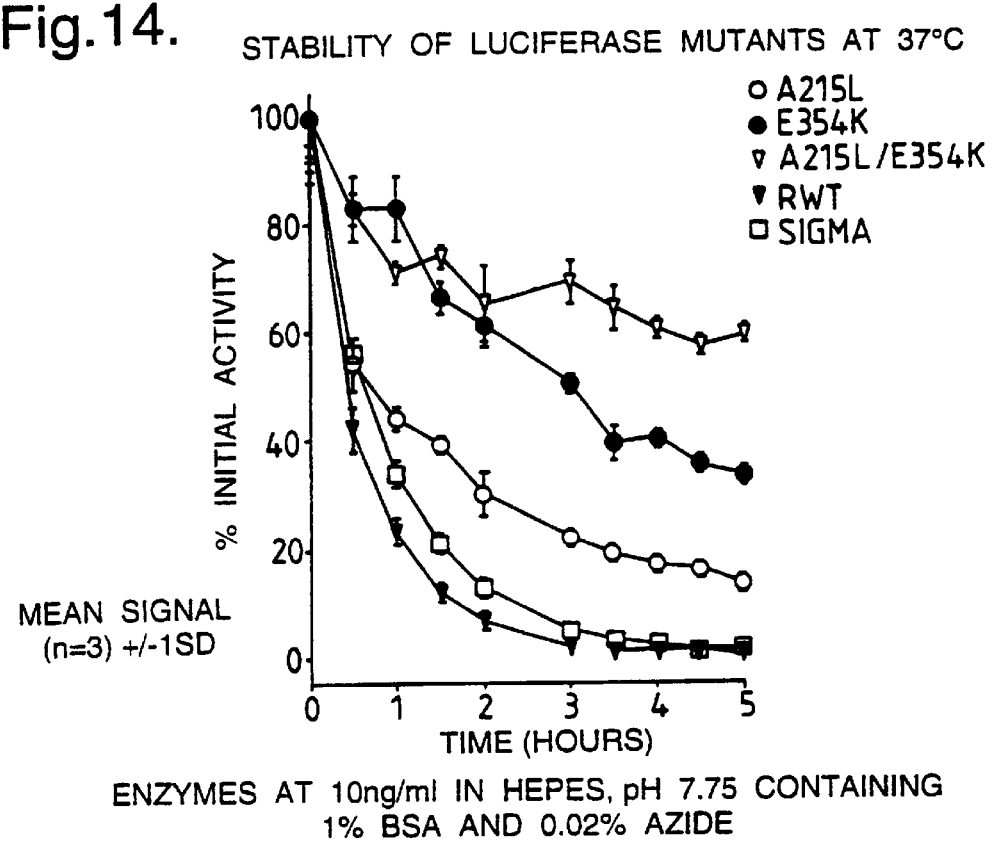

FIG. 14: shows a graph of % initial activity against time of 10 ng/ml of each of the A215L and E354K single, A215L+E354K double, recombinant and Sigma wild-type luciferases over 5 hours in HEPES, pH7.75 containing 1% BSA and 0.02% azide at 37° C.

Figure 15:
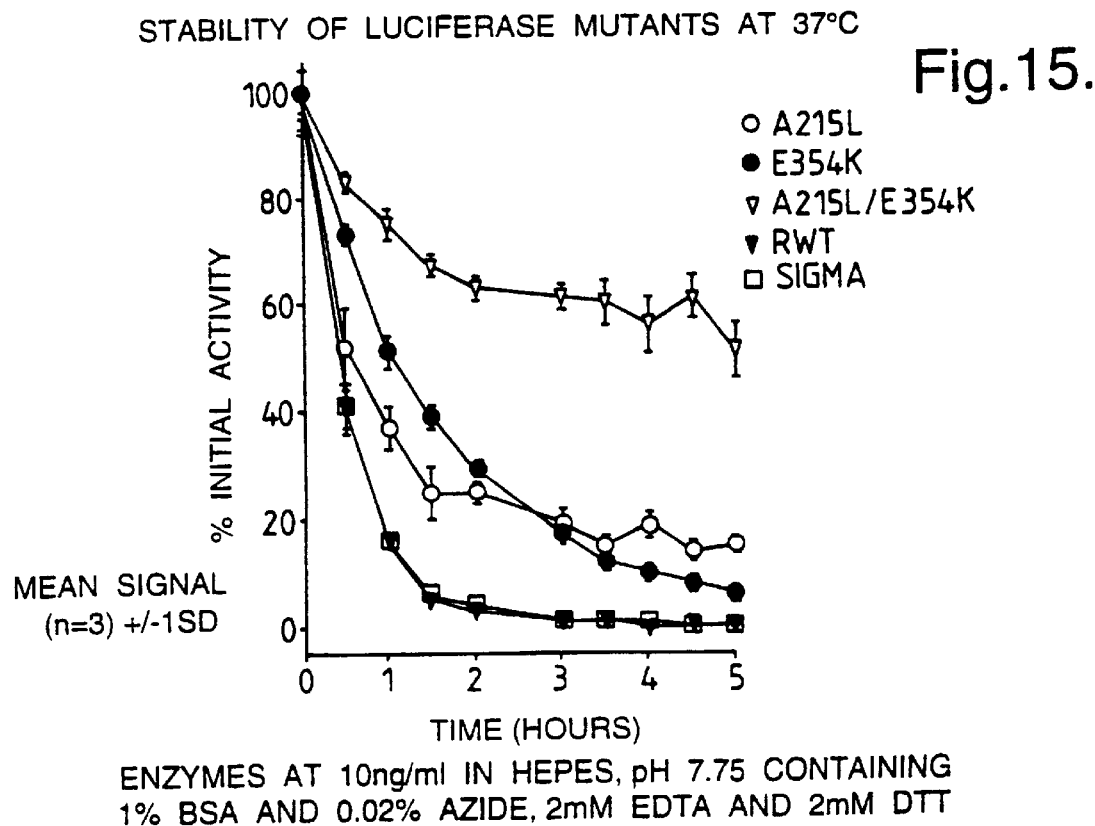

FIG. 15: shows a graph of % initial activity against time of 10 ng/ml of each of the A215L and E354K single, A215L+E354K double, recombinant and Sigma wild-type luciferase over 5 hours in HEPES pH7.75 containing 1% BSA. 0.02% azide, 2 mM EDTA and 2 mM DTT at 37° C.

SEQUENCE LISTING

The sequence listing provided at the end of this specification describes DNA and amino acid sequences as follows:

SEQ ID NO 1: shows the DNA sequence of a DNA encoding for luciferase of the invention wherein the *Photinus pyralis* wild-type codon at 1063 to 1065 is mutated; for lysine the base at 1063 is mutated to an A.

SEQ ID No 2: shows the amino acid sequence of a protein of the invention wherein the *Photinus pyralis* wild-type amino acid 354 glutamate has been changed to another amino acid.

SEQ ID No 3: shows the sequence of the oligonucleotide used for the SDM mutation of pPW601 to give a lysine instead of glutamate at position 354 in Example 2.

SEQ ID No 4: shows the sequence of the oligonucleotide used for the SDM mutation of pPW601 to give leucine at position 215 in Example 5.

SEQ ID No 5: shows the amino acid sequence of a protein of the invention wherein the *Photinus pyralis* wild-type amino acid 354 glutamate has been changed to any other amino acid and the 215 amino acid changed to a leucine.

EXAMPLES

Example 1

Production of Plasmids Containing DNA of the Invention

Plasmids pKK223-3 and pDR540 were obtained from Boehringer Mannheim; pDR540 is also available from Pharmacia.

Plasmid pT7-7 (see Current protocols in Molecular Biology Vol II Section 16.2.1) was obtained from Stan Tabor, Dept of Biol Chem, Harvard Medical School, Boston, Mass. 02115 and (as shown in FIG. 8) contains T7 RNA polymerase promoter φ10 and the translation start site for the T7 gene 10 protein (T7 bp 22857 to 22972) inserted between the PvuII and ClaI sites of pT7-5. Unique restriction sites for creation of fusion proteins (after filling in 5' ends) are Frame 0: EcoR1; Frame 1: NdcI, SmaI, ClaI; Frame 2: BamHI, SalI, HindIII. SacI site of the original polylinker is removed by deletion and an additional XbaI site is provided upstream of the start codon.

Firefly luciferase (prepared from a crystalline suspension, Cat No L9009), coenzyme A and ATP were obtained from Sigma Chemical Co. Beetle luciferin potassium salt was obtained from Promega. Cell extracts were prepared as described in the Promega technical bulletin No 101. Aliquots of *E. coli* cultures were lysed in cell culture lysis reagent (25 mM Tris-phosphate, pH7.8, 2 mM DTT, 2 mM EDTA, 10% glycerol, 1% Triton X-100, 2.5 mg/ml BSA, 1.25 mg/ml lysozyme) for 10 minutes at room temperature and then stored on ice prior to assay.

Luciferase activity of cell lines was assayed by monitoring bioluminescence emitted by colonies by transferring these to nylon filters (Hybond N, Amersham) and then soaking the filters with 0.5 mM luciferin in 100 mM sodium citrate buffer pH5.0 (Wood & DeLuca, (1987) Anal Biochem 161 p501–507). Luciferase assays in vitro were performed at 25° C. using 125 µl of assay buffer (20 mM Tricine, 1 mM MgSo$_4$, 0.1 mM EDTA, 33.3 mM DTT, 0.27 mM coenzyme A, 0.47 mM luciferin, 0.53 mM ATP and 1 to 2 µl of sample). The final pH of the assay cocktail was 7.8 and light measurements were made with a BioOrbit 1250 luminometer.

For production of non-specific chemical mutations of DNA, plasmids containing luc genes were treated according to the method of Kironde et al (1989) Biochem. J. 259. p421–426 using 0.8M hydroxylamine, 1 mM EDTA in 0.1 mM sodium phosphate pH6.0 for 2 hours at 65° C. The mutagenised plasmid was desalted on a G60 DNA grade Nick column (Pharmacia) followed by transformation into *E. coli* BL21(DE3).

Heat inactivation studies were carried out by incubating crude cell extracts having luciferase activity at various temperatures for 20 minutes and measuring remaining activities. In studies with the purified luciferase obtained from Sigma the enzyme was diluted in Promega lysis buffer prior to inactivation. For time dependent studies Eppendorf tubes containing 50 µl of crude cell extract or Sigma luciferase in lysis buffer were incubated at 37° C. At various times a tube was removed and cooled on ice prior to assay. The remaining activity was expressed as per cent of original activity.

Relative levels of expression of luciferase from each of the constructs pPW204, pPW116 and pPW304 are 0.1:0.5:1.0 from *E. coli* BL21(DE3). Cells were grown in LB at 37° C. to an OD 600 of 0.3 then induced with IPTG and growth allowed to continue for 4 hours after which crude extract was prepared and luciferase activity measured.

TABLE 1: Ribosome binding sites (underlined) and start codons in the expression constructs used in Example 1.

pPW304 <u>AAGGAG</u>ATATACAT ATG* CGT AGA ATT CAA ATG pPW116 <u>AGGA</u>AAC<u>AGGA</u>TCCA ATG* pPW204 <u>AGGA</u>CAGCAA ATG*

The site directed mutagenesis required to convert the glutamate to an alternative amino acid was carried out using the following protocol. Because the glutamate to lysine mutation lies within a unique AvaI restriction site, and thus destroys it, it is possible to use a single oligonucleotide as the mutagenic and selection oligonucleotide.

Site Directed Mutagenesis Protocol:

Plasmid selected is denatured and annealed with a selection/mutagenic oligonucleotide for lysine: 5'-CATCCCCCT<u>T</u>GGGTGTAATCAG-3' with the underlined T being the mismatch. The mutant DNA strand is synthesised and ligated and the whole primary restriction digested with AvaI.

Transformation into cells, here *E. coli* BMH 71-18 mut S cells, was carried out using a Bio-Rad Gene Pulser version 2-89. Harvested cells and purified mixed plasmid pool containing mutated and parental plasmids were provided and secondary restriction digest with AvaI was carried out before transformation into *E. coli* JM109 cells. These cells were plated on selective media (LB agar+50 µg/ml ampicillin) and clones screened by purifying their plasmid DNA and analysing for the loss of the AvaI restriction site. Plasmid DNA was purified in each case using the alkaline lysis method of Birnboim and Doly (1979) Nucleic Acids Research 7, p1513. Precise protocols were as described in the Transformer®™ Site-Directed Mutagenesis Kit (Version 2) sold by Clontech Laboratories Inc (US) catalog No K1600-1.

The restriction map for pPW601a, a variant of pPW116 derived from Pharmacia pDR540 and BamH1/Sst1 fragment from pGEM-luc with the Xho site destroyed is shown as FIG. 4. Site directed mutagenesis was carried out as described above and in the Clontech instructions such as to convert the wild-type Photinus luc gene inserted therein into a sequence as shown in SEQ ID No 1 wherein 1063–1065 is AAG, with expressed protein of amino acid sequence modified at position 354 as shown in SEQ ID No 2 to Lysine.

Example 2

Heat Stability of Luciferases

The heat stability of various luciferases expressed by unmodified and modified (ie. of the invention) luc genes in vectors in *E. coli* produced as described above was determined and results are shown in FIGS. 5 to 8.

A comparison of $t^{1/2}$ (half-life) of the activity of 50 μg/ml luciferase at 43.5° C. in 50 mM potassium phosphate buffer pH7.8, 1 mM EDTA, 0.2% (w/v) BSA, 1 mM DTT and 10% ammonium sulphate shows 50% activity remaining to be reached at times as follows:

| | |
|---|---|
| Sigma wildtype luciferase: | $t^{1/2}$ reached in approximately 1.5 minutes |
| pPW601 (354 = glutamate): | $t^{1/2}$ reached in approximately 5 minutes |
| pPW601aK (354 = lysine): | $t^{1/2}$ reached in approximately 30 minutes |

Thus clearly from the aforesaid figures it can be seen that replacing the 354 glutamate with lysine increases heat stability of luciferase at least up to 43.5° C.

Example 3

Heat Stability of Luciferase

The heat stability of a number of luciferases expressed by SDM modified luc genes corresponding to other position 354 mutations of the invention in vectors in *E. coli* produced by methods analogous to that as described in Example 1 was determined and results are graphically shown in FIG. 10.

A comparison of $t^{1/2}$ at 40° C. in Promega lysis buffer was carried out and results obtained in $t^{1/2}$ in minutes as:

| | |
|---|---|
| pPW601aK (354 = lysine) | $t^{1/2}$ reached in approximately 13 minutes |
| pPW601aR (354 = arginine) | $t^{1/2}$ reached in approximately 13 minutes |
| pPW601aL (354 = leucine) | $t^{1/2}$ reached in approximately 10 minutes |
| pPW601aI (354 = isoleucine) | $t^{1/2}$ reached in approximately 10 minutes |
| pPW601aN (354 = asparagine) | $t^{1/2}$ reached in approximately 10 minutes |
| pPW601aV (354 = valine) | $t^{1/2}$ reached in approximately 9 minutes |
| pPW601aW (354 = tryptophan) | $t^{1/2}$ reached in approximately 8 minutes |
| pPW601aA (354 = alanine) | $t^{1/2}$ reached in approximately 6.5 minutes |
| pPW601aY (354 = tyrosine) | $t^{1/2}$ reached in approximately 6.5 minutes |
| pPW601aM (354 = methionine) | $t^{1/2}$ reached in approximately 5.5 minutes |
| pPW601aF (354 = phenylalanine) | $t^{1/2}$ reached in approximately 5 minutes |
| pPW601aH (354 = histidine) | $t^{1/2}$ reached in approximately 5 minutes |
| pPW601aT (354 = threonine) | $t^{1/2}$ reached in approximately 4.5 minutes |
| pPW601aQ (354 = glutamine) | $t^{1/2}$ reached in approximately 4.5 minutes |
| pPW601aC (354 = cysteine) | $t^{1/2}$ reached in approximately 4 minutes |
| pPW601aS (354 = serine) | $t^{1/2}$ reached in approximately 3.5 minutes |
| pPW601aE (354 = glutamic acid) | $t^{1/2}$ reached in approximately 1 minutes |
| pPW601aD (354 = aspartic acid) | $t^{1/2}$ reached in approximately 1 minutes |
| pPW601aP (354 = proline) | $t^{1/2}$ reached in approximately 1 minutes |
| pPW601aG (354 = glycine) | $t^{1/2}$ reached in approximately <1 minutes |

Example 4

Stability of Luciferases at 37° C. and Room Temperature

Luciferases of pPW601K lysine mutation (86 ng/ml), recombinant wild type (550 ng/ml) and native type (Sigma) (62.5 ng/ml) were incubated for 4 hours at 37° C. in 1% BSA, pH7.75 HEPES buffer with 0.02% azide as preservative. To measure remaining activity 1ng luciferase was added to D-luciferin substrate and luminescent counts per minute recorded.

Results are shown below in terms of remaining activity after incubation for 2 hours at 37° C. and after 10 days at room temperature.

After 2 hours at 37° C.:

| After 2 hours at 37° C. | |
|---|---|
| E354K mutant luciferase | 70% remaining activity |
| Recombinant Wild Type luciferase | 12% remaining activity |
| Sigma Native luciferase | 18% remaining activity |
| After 10 days at Room temperature: | |
| E354K mutant luciferase | 85% remaining activity |
| Recombinant Wild Type luciferase | 59% remaining activity |
| Sigma Native luciferase | 71% remaining activity |

Example 5

Preparation and Stability of 354K:215L Double Mutant

The double mutant 354 Lysine:215 Leucine of pPW601a *Photinus pyralis* luciferase was prepared by taking pPW601aE354K as described in Example 1 and mutating it using the oligonucleotide of SEQ ID No 4 5'-GAATCTGACGCAG<u>AG</u>AGTTCTATGCGG-3', wherein the underlined bases represent the mismatches that cause the mutation. This mutation was confirmed by DNA sequencing and measurement of the thermostability of the resultant luciferase as expressed in *E. coli* by a method analogous to that as described in Example 1 was carried out as in Examples 2 to 4 using pH7.8 phosphate buffer containing 1 mM EDTA, 0.2% (w/v) BSA, 1 mM DTT and 10% ammonium sulphate as heat inactivation medium.

At 43.5° C. in the phosphate buffer there was less than 5% loss of activity over 32 minutes, while at 47° C. $t^{1/2}$ was approximately 38 minutes. At 50° C. the double mutant retains 15% activity after 16 minutes incubation. Results for this inactivation test are shown graphically in FIG. 12.

Example 6

Purification of Luciferases

*E. coli* JM109 cells expressing the recombinant wild-type or mutant luciferases were grown at 30° C. in Luria Broth (LB) containing 50 μg/ml ampicillin and induced with IPTG (1 mM) during early log phase. Cells were harvested in mid stationary phase and resuspended in 50 mM Tris-HCl pH8.0 containing 50 mM KCl, 1 mM dithiothreitol, 1.2 mM phenylmethylsulphonylfluoride (PMSF) and 1 mM EDTA (Buffer A). Cells were broken by disruption in an MSE soniprep 150 sonicator (amplitude 14μ) and the cell lysate centrifuged at 30000×g for 30 minutes. The supernatant of the crude extract was then subjected to fractionation with ammonium sulphate with the fraction precipitated between 35% and 55% saturation being found to contain luciferase activity and being dissolved in Buffer A.

The extract was desalted using a Pharmacia PD10 column equilibrated in 50 mM Tris-HCl pH8.0 containing 0.5 mM DTT (Buffer B) and the desalted extract applied to a Pharmacia Mono Q anion-exchange column and eluted with a linear gradient of 0 to 500 mM NaCl in Buffer B at a flow rate of 4 ml/minute in 2 ml fractions. The peak fraction of luciferase activity was collected and dialysed against 25 mM sodium phosphate buffer. pH7.5, containing 0.5 mM DTT and 12% (v/v) glycerol for long term storage.

Example 7

Heat Inactivation of Purified Luciferases

Eppendorf tubes containing cell free extracts of luciferase were prepared as described in Example 6. Purified preparations of luciferase (50 μg/ml) were incubated in thermostability buffer comprising 50 mM potassium phosphate buffer pH7.8 containing 10% saturated ammonium sulphate, 1 mM dithiothreitol and 0.2% bovine serum albumin (BSA). At set times a tube was removed and cooled in an ice/water bath prior to assay with remaining assayed activity being calculated as a percentage of the initial activity.

Arrhenius plots for purified recombinant wild-type and thermostable luciferases were constructed by measuring the half-life for inactivation in thermostability buffer over a range of temperatures from 42° C. to 50° C. The natural log of t½ in minutes was then plotted against 1/K. For an equivalent rate of inactivation the E354K mutation increases thermostability by 2° C. at temperatures in this range as compared with an increase of 5° C. with the A215L mutation and 6° C. for the double mutant E354K+A215L; the latter showing the additive nature of the double mutation.

Example 8

Increased Expression of Mutant Luciferases as Compared to Wild-type Recombinant Luciferase in E. coli Expression of luciferase in E. coli JM109 cells was monitored during growth in liquid culture at 37° C. Cells expressing the thermostable mutants being found to accumulate more active luciferase during growth than cells expressing the recombinant wild-type enzyme. FIG. 13 shows this effect graphically in plotting luciferase activity with increasing optical density at 600 nm for cultures of recombinant wild-type, E354K+A215L double mutant and E354K. It can be seen that the increased thermostability of the single and double mutant allows increased production of luciferase at the 37° C. culture temperature.

Example 9

Effect of Buffer on Stability of Mutant Luciferases at 37° C.

10 ng/ml solutions of each of the A215L, E354K, E354+A215L, recombinant wild-type and sigma luciferases were prepared in HEPES pH7.75 buffer with 1% BSA and 0.02% azide and thermostability at 37° C. compared to that of the same compositions with addition of 2 mM EDTA and 2 mMDTT. Results are shown graphically in FIGS. 14 and 15 indicating that the relative stability of A215L and E354K varies with buffer at 37° C.

Example 10

Effect of Amino Acid Substitution on Wavelength of Light Emitted in Oxidation of D-luciferin The wavelength of light emitted on oxidation of D-luciferin with the various luciferases of the invention set out in Example 3 was measured and found to vary with the amino acid mutation. The wavelength of light emitted varied 5 nm between recombinant wild-type (E354) and E354K, and about 15 nm between E354K and E354I.

Wild-type recombinant E. coli organisms give a yellow green lumineasence in the presence of D-luciferin. Colours emitted by the respective mutant E. coli when provided with D-luciferin were as follows:

| | |
|---|---|
| E354G | yellow-green |
| E354N | yellow-green |
| E354A | green |
| E354V | orange-red |
| E354M | orange-red |
| E354F | yellow-green |
| E354L | yellow |
| E354Y | yellow-green |
| E354S | yellow-green |
| E354C | yellow-green |
| E354K | yellow |
| E354Q | yellow-green |
| E354W | yellow-green |
| E354T | yellow-green |
| E354P | orange |
| E354R | yellow-orange |
| E354H | yellow-green |
| E354N | yellow |
| E354I | red |

We claim:

1. An isolated protein having luciferase activity which protein has over 60% amino acid sequence homology to the luciferase from *Photinus pyralis, Luciola mingrelica, Luciola cruciata*, or *Luciola lateralis* and includes the amino acid sequence XGDDKPGA wherein X is an amino acid residue other than glutamate, glycine, proline or aspartic acid.

2. An isolated protein as claimed in claim 1 which includes the amino acid sequence TPXGDDKPGA where X is an amino acid residue other than glutamate, glycine, proline or aspartic acid.

3. An isolated protein as claimed in claim 1 wherein X is selected from the group consisting of tryptophan, valine, leucine, isoleucine and asparagine or an analogue or modification of any of these.

4. An isolated protein as claimed in claim 1 wherein X is selected from the group consisting of lysine and arginine or an analogue or modification of any of these.

5. An isolated protein as claimed in claim 1 wherein said protein is a firefly or glow-worm protein.

6. An isolated DNA encoding a protein as claimed in claim 1.

7. A vector comprising a luc gene encoding for a protein as claimed in claim 1.

8. An isolated protein according to claim 1 wherein said protein is a Photinus or Luciola luciferase.

9. An isolated DNA according to claim 6 having the sequence of SEQ ID NO: 1.

10. An isolated DNA encoding a protein as claimed in claim 2.

11. An isolated DNA according to claim 6 wherein said protein is a luciferase from one of Photinus or Luciola.

12. A vector of claim 7 selected from the group consisting of pKK223-3, pDR540 and pT7-7 into which said luc gene has been ligated.

13. A vector comprising a DNA according to claim 6.

14. A vector comprising a DNA according to claim 9.

15. A vector comprising a DNA according to claim 10.

16. A vector comprising a DNA according to claim 11.

17. An isolated cell comprising a vector according to claim 7.

18. An isolated cell capable of expressing a protein according to claim 1.

19. A cell according to claim 17 wherein said cell is an *E. coli, S. cerevisiae* or insect cell.

20. A cell according to claim 18 wherein said cell is an *E. coli, S. cerevisiae* or insect cell.

21. An assay method comprising measuring ATP using luciferin and a protein of claim 1 to generate light, the quantity of which is related to the amount of ATP present.

22. An assay according to claim 21 wherein said assay is carried out at a temperature of from 30° C. to 70° C.

23. An assay according to claim 22 wherein said temperature is in the range of 37° C. to 60° C.

24. An assay according to claim 23 wherein said temperature is in the range of 40° C. to 50° C.

25. A test kit comprising a specific binding reagent labeled with a protein according to claim 1.

26. A method of increasing the heat stability of a protein having luciferase activity, which protein has over 60% amino acid sequence homology to the luciferase from *Photinus pyralis, Luciola mingrelica, Luciola cruciata*, or *Luciola lateralis*, and comprises an amino acid sequence XGDDKPGA, said method comprising replacing X with an amino acid, analogue or modification thereof which is different from glutamate, glycine, proline, or aspartic acid.

27. In a luciferase which has over 60% amino acid sequence homology to the luciferase from *Photinus pyralis, Luciola mingrelica, Luciola cruciata*, or *Luciola lateralis*, is thermally stable to a temperature of about 30° C. and comprises an amino acid sequence XGDDKPGA, the improvement comprising an amino acid other than glutamate, glycine, proline or aspartic acid as a replacement for X.

28. An isolated and purified protein comprising the amino acid sequence of SEQ ID NO:2 wherein Xaa is one of tryptophan, valine, leucine, isoleucine, asparagine, lysine and arginine or an analogue or modification of these.

29. An isolated and purified DNA encoding a protein of claim 28.

30. A vector comprising a DNA of claim 29.

31. An isolated and purified cell comprising the vector of claim 30.

32. An assay method comprising measuring ATP using luciferin and luciferase to generate light, the quantity of which is related to the amount of ATP characterized, said luciferase being a protein according to claim 28.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
        (A) LENGTH: 1722 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 1:

```
CAAATGGAAG ACGCCAAAAA CATAAAGAAA GGCCCGGCGC CATTCTATCC TCTAGAGGAT        60
GGAACCGCTG GAGAGCAACT GCATAAGGCT ATGAAGAGAT ACGCCCTGGT TCCTGGAACA       120
ATTGCTTTTA CAGATGCACA TATCGAGGTG AACATCACGT ACGCGGAATA CTTCGAAATG       180
TCCGTTCGGT TGGCAGAAGC TATGAAACGA TATGGGCTGA ATACAAATCA CAGAATCGTC       240
GTATGCAGTG AAAACTCTCT TCAATTCTTT ATGCCGGTGT TGGGCGCGTT ATTTATCGGA       300
GTTGCAGTTG CGCCCGCGAA CGACATTTAT AATGAACGTG AATTGCTCAA CAGTATGAAC       360
ATTTCGCAGC CTACCGTAGT GTTTGTTTCC AAAAAGGGGT TGCAAAAAAT TTGAACGTG        420
CAAAAAAAT TACCAATAAT CCAGAAAATT ATTATCATGG ATTCTAAAAC GGATTACCAG        480
GGATTTCAGT CGATGTACAC GTTCGTCACA TCTCATCTAC CTCCCGGTTT TAATGAATAC       540
GATTTTGTAC CAGAGTCCTT TGATCGTGAC AAAACAATTG CACTGATAAT GAATTCCTCT       600
GGATCTACTG GGTTACCTAA GGGTGTGGCC CTTCCGCATA GAACTGCCTG CGTCAGATTC       660
TCGCATGCCA GAGATCCTAT TTTTGGCAAT CAAATCATTC CGGATACTGC GATTTTAAGT       720
GTTGTTCCAT TCCATCACGG TTTTGGAATG TTTACTACAC TCGGATATTT GATATGTGGA       780
TTTCGAGTCG TCTTAATGTA TAGATTTGAA GAAGAGCTGT TTTTACGATC CCTTCAGGAT       840
TACAAAATTC AAAGTGCGTT GCTAGTACCA ACCCTATTTT CATTCTTCGC CAAAAGCACT       900
CTGATTGACA AATACGATTT ATCTAATTTA CACGAAATTG CTTCTGGGGG CGCACCTCTT       960
TCGAAAGAAG TCGGGGAAGC GGTTGCAAAA CGCTTCCATC TTCCAGGGAT ACGACAAGGA      1020
TATGGGCTCA CTGAGACTAC ATCAGCTATT CTGATTCACA CCNNNGGGGA TGATAAACCG      1080
GGCGCGGTCG GTAAAGTTGT TCCATTTTTT GAAGCGAAGG TTGTGGATCT GGATACCGGG      1140
AAAACGCTGG GCGTTAATCA GAGAGGCGAA TTATGTGTCA GAGGACCTAT GATTATGTCC      1200
GGTTATGTAA ACAATCCGGA AGCGACCAAC GCCTTGATTG ACAAGGATGG ATGGCTACAT      1260
TCTGGAGACA TAGCTTACTG GGACGAAGAC GAACACTTCT TCATAGTTGA CCGCTTGAAG      1320
TCTTTAATTA AATACAAAGG ATATCAGGTG GCCCCCGCTG AATTGGAATC GATATTGTTA      1380
CAACACCCCA ACATCTTCGA CGCGGGCGTG GCAGGTCTTC CCGACGATGA CGCCGGTGAA      1440
CTTCCCGCCG CCGTTGTTGT TTTGGAGCAC GGAAAGACGA TGACGGAAAA AGAGATCGTG      1500
GATTACGTCG CCAGTCAAGT AACAACCGCG AAAAAGTTGC GCGGAGGAGT TGTGTTTGTG      1560
GACGAAGTAC CGAAAGGTCT TACCGGAAAA CTCGACGCAA GAAAAATCAG AGAGATCCTC      1620
ATAAAGGCCA AGAAGGGCGG AAAGTCCAAA TTGTAAAATG TAACTGTATT CAGCGATGAC      1680
GAAATTCTTA GCTATTGTAA TCCTCCGAGG CCTCGAGGTC GA                        1722
```

(2) INFORMATION FOR SEQ ID NO: 2:

(i) SEQUENCE CHARACTERISTICS:
        (A) LENGTH: 550 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 2:

| Met | Glu | Asp | Ala | Lys | Asn | Ile | Lys | Lys | Gly | Pro | Ala | Pro | Phe | Tyr | Pro |
|---|---|---|---|---|---|---|---|---|---|---|---|---|---|---|---|
| 1 | | | | 5 | | | | | 10 | | | | | 15 | |

| Leu | Glu | Asp | Gly | Thr | Ala | Gly | Glu | Gln | Leu | His | Lys | Ala | Met | Lys | Arg |
|---|---|---|---|---|---|---|---|---|---|---|---|---|---|---|---|
| | | | 20 | | | | | 25 | | | | | 30 | | |

| Tyr | Ala | Leu | Val | Pro | Gly | Thr | Ile | Ala | Phe | Thr | Asp | Ala | His | Ile | Glu |
|---|---|---|---|---|---|---|---|---|---|---|---|---|---|---|---|
| | | 35 | | | | | 40 | | | | | 45 | | | |

| Val | Asn | Ile | Thr | Tyr | Ala | Glu | Tyr | Phe | Glu | Met | Ser | Val | Arg | Leu | Ala |
|---|---|---|---|---|---|---|---|---|---|---|---|---|---|---|---|
| | 50 | | | | | 55 | | | | | 60 | | | | |

| Glu | Ala | Met | Lys | Arg | Tyr | Gly | Leu | Asn | Thr | Asn | His | Arg | Ile | Val | Val |
|---|---|---|---|---|---|---|---|---|---|---|---|---|---|---|---|
| 65 | | | | | 70 | | | | | 75 | | | | | 80 |

| Cys | Ser | Glu | Asn | Ser | Leu | Gln | Phe | Phe | Met | Pro | Val | Leu | Gly | Ala | Leu |
|---|---|---|---|---|---|---|---|---|---|---|---|---|---|---|---|
| | | | | 85 | | | | | 90 | | | | | 95 | |

| Phe | Ile | Gly | Val | Ala | Val | Ala | Pro | Ala | Asn | Asp | Ile | Tyr | Asn | Glu | Arg |
|---|---|---|---|---|---|---|---|---|---|---|---|---|---|---|---|
| | | | 100 | | | | | 105 | | | | | 110 | | |

| Glu | Leu | Leu | Asn | Ser | Met | Asn | Ile | Ser | Gln | Pro | Thr | Val | Val | Phe | Val |
|---|---|---|---|---|---|---|---|---|---|---|---|---|---|---|---|
| | | 115 | | | | | 120 | | | | | 125 | | | |

| Ser | Lys | Lys | Gly | Leu | Gln | Lys | Ile | Leu | Asn | Val | Gln | Lys | Lys | Leu | Pro |
|---|---|---|---|---|---|---|---|---|---|---|---|---|---|---|---|
| | 130 | | | | | 135 | | | | | 140 | | | | |

| Ile | Ile | Gln | Lys | Ile | Ile | Ile | Met | Asp | Ser | Lys | Thr | Asp | Tyr | Gln | Gly |
|---|---|---|---|---|---|---|---|---|---|---|---|---|---|---|---|
| 145 | | | | | 150 | | | | | 155 | | | | | 160 |

| Phe | Gln | Ser | Met | Tyr | Thr | Phe | Val | Thr | Ser | His | Leu | Pro | Pro | Gly | Phe |
|---|---|---|---|---|---|---|---|---|---|---|---|---|---|---|---|
| | | | | 165 | | | | | 170 | | | | | 175 | |

| Asn | Glu | Tyr | Asp | Phe | Val | Pro | Glu | Ser | Phe | Asp | Arg | Asp | Lys | Thr | Ile |
|---|---|---|---|---|---|---|---|---|---|---|---|---|---|---|---|
| | | | 180 | | | | | 185 | | | | | 190 | | |

| Ala | Leu | Ile | Met | Asn | Ser | Ser | Gly | Ser | Thr | Gly | Leu | Pro | Lys | Gly | Val |
|---|---|---|---|---|---|---|---|---|---|---|---|---|---|---|---|
| | | 195 | | | | | 200 | | | | | 205 | | | |

| Ala | Leu | Pro | His | Arg | Thr | Ala | Cys | Val | Arg | Phe | Ser | His | Ala | Arg | Asp |
|---|---|---|---|---|---|---|---|---|---|---|---|---|---|---|---|
| | 210 | | | | | 215 | | | | | 220 | | | | |

| Pro | Ile | Phe | Gly | Asn | Gln | Ile | Ile | Pro | Asp | Thr | Ala | Ile | Leu | Ser | Val |
|---|---|---|---|---|---|---|---|---|---|---|---|---|---|---|---|
| 225 | | | | | 230 | | | | | 235 | | | | | 240 |

| Val | Pro | Phe | His | His | Gly | Phe | Gly | Met | Phe | Thr | Thr | Leu | Gly | Tyr | Leu |
|---|---|---|---|---|---|---|---|---|---|---|---|---|---|---|---|
| | | | | 245 | | | | | 250 | | | | | 255 | |

| Ile | Cys | Gly | Phe | Arg | Val | Val | Leu | Met | Tyr | Arg | Phe | Glu | Glu | Glu | Leu |
|---|---|---|---|---|---|---|---|---|---|---|---|---|---|---|---|
| | | | 260 | | | | | 265 | | | | | 270 | | |

| Phe | Leu | Arg | Ser | Leu | Gln | Asp | Tyr | Lys | Ile | Gln | Ser | Ala | Leu | Leu | Val |
|---|---|---|---|---|---|---|---|---|---|---|---|---|---|---|---|
| | | 275 | | | | | 280 | | | | | 285 | | | |

| Pro | Thr | Leu | Phe | Ser | Phe | Phe | Ala | Lys | Ser | Thr | Leu | Ile | Asp | Lys | Tyr |
|---|---|---|---|---|---|---|---|---|---|---|---|---|---|---|---|
| | 290 | | | | | 295 | | | | | 300 | | | | |

| Asp | Leu | Ser | Asn | Leu | His | Glu | Ile | Ala | Ser | Gly | Gly | Ala | Pro | Leu | Ser |
|---|---|---|---|---|---|---|---|---|---|---|---|---|---|---|---|
| 305 | | | | | 310 | | | | | 315 | | | | | 320 |

| Lys | Glu | Val | Gly | Glu | Ala | Val | Ala | Lys | Arg | Phe | His | Leu | Pro | Gly | Ile |
|---|---|---|---|---|---|---|---|---|---|---|---|---|---|---|---|
| | | | | 325 | | | | | 330 | | | | | 335 | |

| Arg | Gln | Gly | Tyr | Gly | Leu | Thr | Glu | Thr | Thr | Ser | Ala | Ile | Leu | Ile | Thr |
|---|---|---|---|---|---|---|---|---|---|---|---|---|---|---|---|
| | | | 340 | | | | | 345 | | | | | 350 | | |

| Pro | Xaa | Gly | Asp | Asp | Lys | Pro | Gly | Ala | Val | Gly | Lys | Val | Val | Pro | Phe |
|---|---|---|---|---|---|---|---|---|---|---|---|---|---|---|---|
| | | 355 | | | | | 360 | | | | | 365 | | | |

| Phe | Glu | Ala | Lys | Val | Val | Asp | Leu | Asp | Thr | Gly | Lys | Thr | Leu | Gly | Val |
|---|---|---|---|---|---|---|---|---|---|---|---|---|---|---|---|
| | 370 | | | | | 375 | | | | | 380 | | | | |

| Asn | Gln | Arg | Gly | Glu | Leu | Cys | Val | Arg | Gly | Pro | Met | Ile | Met | Ser | Gly |
|---|---|---|---|---|---|---|---|---|---|---|---|---|---|---|---|
| 385 | | | | | 390 | | | | | 395 | | | | | 400 |

```
Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ser Lys Leu
545                 550
```

(2) INFORMATION FOR SEQ ID NO: 3:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 3:

CATCCCCCTT GGGTGTAATC AG                          22

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 4:

GAATCTGACG CAGAGAGTTC TATGCGG                    27

(2) INFORMATION FOR SEQ ID NO: 5:

(i) SEQUENCE CHARACTERISTICS:
        (A) LENGTH: 550 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 5:

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30
```

-continued

```
Tyr Ala Leu Val Pro Gly Thr Ile Ala Phe Thr Asp Ala His Ile Glu
         35                  40                  45
Val Asn Ile Thr Tyr Ala Glu Tyr Phe Glu Met Ser Val Arg Leu Ala
 50                  55                  60
Glu Ala Met Lys Arg Tyr Gly Leu Asn Thr Asn His Arg Ile Val Val
 65                  70                  75                  80
Cys Ser Glu Asn Ser Leu Gln Phe Phe Met Pro Val Leu Gly Ala Leu
                 85                  90                  95
Phe Ile Gly Val Ala Val Ala Pro Ala Asn Asp Ile Tyr Asn Glu Arg
                100                 105                 110
Glu Leu Leu Asn Ser Met Asn Ile Ser Gln Pro Thr Val Val Phe Val
             115                 120                 125
Ser Lys Lys Gly Leu Gln Lys Ile Leu Asn Val Gln Lys Lys Leu Pro
130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
        195                 200                 205
Ala Leu Pro His Arg Thr Leu Cys Val Arg Phe Ser His Ala Arg Asp
    210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
        275                 280                 285
Pro Thr Leu Phe Ser Phe Phe Ala Lys Ser Thr Leu Ile Asp Lys Tyr
    290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Xaa Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
    370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
            420                 425                 430
Phe Ile Val Asp Arg Leu Lys Ser Leu Ile Lys Tyr Lys Gly Tyr Gln
        435                 440                 445
```

-continued

```
Val Ala Pro Ala Glu Leu Glu Ser Ile Leu Leu Gln His Pro Asn Ile
        450             455             460

Phe Asp Ala Gly Val Ala Gly Leu Pro Asp Asp Asp Ala Gly Glu Leu
465             470             475             480

Pro Ala Ala Val Val Val Leu Glu His Gly Lys Thr Met Thr Glu Lys
            485             490             495

Glu Ile Val Asp Tyr Val Ala Ser Gln Val Thr Thr Ala Lys Lys Leu
            500             505             510

Arg Gly Gly Val Val Phe Val Asp Glu Val Pro Lys Gly Leu Thr Gly
        515             520             525

Lys Leu Asp Ala Arg Lys Ile Arg Glu Ile Leu Ile Lys Ala Lys Lys
        530             535             540

Gly Gly Lys Ser Lys Leu
545             550
```